United States Patent
Kim et al.

(10) Patent No.: US 9,040,106 B2
(45) Date of Patent: May 26, 2015

(54) PHARMACEUTICAL COMPOSITION FOR PREVENTING OR TREATING DIABETIC ERECTILE DYSFUNCTION COMPRISING C3G OR EXTRACT OF MULBERRY CONTAINING C3G

(75) Inventors: Sae-Woong Kim, Seongnam-si (KR); Myung-Hoon Chun, Yongin-si (KR); In-Beom Kim, Seongnam-si (KR); U-Syn Ha, Seoul (KR); Su-Jin Kim, Namyangju-si (KR); Woong-Jin Bae, Seoul (KR); Yong-Sun Choi, Seoul (KR)

(73) Assignee: CATHOLIC UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/342,004

(22) PCT Filed: Mar. 22, 2012

(86) PCT No.: PCT/KR2012/002080
§ 371 (c)(1),
(2), (4) Date: Feb. 28, 2014

(87) PCT Pub. No.: WO2013/032087
PCT Pub. Date: Mar. 7, 2013

(65) Prior Publication Data
US 2014/0242204 A1 Aug. 28, 2014

(30) Foreign Application Priority Data
Aug. 30, 2011 (KR) .................. 10-2011-0087384

(51) Int. Cl.
*A61K 31/7048* (2006.01)
*A61K 36/605* (2006.01)

(52) U.S. Cl.
CPC ........... *A61K 31/7048* (2013.01); *A61K 36/605* (2013.01)

(58) Field of Classification Search
None
See application file for complete search history.

(56) References Cited

U.S. PATENT DOCUMENTS

2005/0084548 A1 4/2005 Tsuda

FOREIGN PATENT DOCUMENTS

| CN | 101204464 A | * | 6/2008 |
| KR | 10-2005-0024796 | | 3/2005 |
| KR | 10-2008-0054984 | | 6/2008 |
| KR | 2008-0092060 | | 10/2008 |
| KR | 10-2010-0012723 | | 2/2010 |
| KR | 10-2010-0078448 | | 7/2010 |
| KR | 10-2011-0014401 | | 2/2011 |
| KR | 10-2011-0067813 | | 6/2011 |
| WO | 2008/126979 | | 10/2008 |

OTHER PUBLICATIONS

Fedelle, Domenico et al., "Erectile dysfunction in Type 1 and Type 2 diabetics in Italy," International Journal of Epidemiology, vol. 29, Issue 3, p. 524-531 (Jun. 2000).
Johannes, C. B. et al., "Incidence of erectile dysfunction in men 40 to 69 years old: longitudinal results from the Massachusetts male aging study," J. Urol. 163, 460-463 (Feb. 2000) abstract.
Kim HB, et al. "The Development of Natural Pigment with Mulberry Fruit as a Food Additive," Korean Journal Crop Science. 56 (1) p. 18-22 (Mar. 2011).
SBS News, [Good economy] Fresh 'mulberry jam and mulberry dressing,' Jun. 30, 2009, Reported by Park ji-eun.

* cited by examiner

*Primary Examiner* — Susan Hoffman
(74) *Attorney, Agent, or Firm* — Lexyoume IP Meister, PLLC

(57) ABSTRACT

The present invention relates to the ameliorating effects of C3G (Cyanidin-3-O-β-d-glucopyranoside) on diabetic erectile dysfunction. In particular, the present invention relates to a pharmaceutical composition and food composition for preventing or treating diabetic erectile dysfunction comprising C3G. In addition, the present invention relates to a pharmaceutical composition and food composition for preventing or treating diabetic erectile dysfunction comprising extract of mulberry containing C3G.

8 Claims, 3 Drawing Sheets

PHARMACEUTICAL COMPOSITION FOR PREVENTING OR TREATING DIABETIC ERECTILE DYSFUNCTION COMPRISING C3G OR EXTRACT OF MULBERRY CONTAINING C3G

TECHNICAL FIELD

The present invention relates to the ameliorating effects of C3G (Cyanidin-3-O-β-d-glucopyranoside) on diabetic erectile dysfunction. In particular, the present invention relates to a pharmaceutical composition and food composition for preventing or treating diabetic erectile dysfunction comprising C3G. In addition, the present invention relates to a pharmaceutical composition and food composition for preventing or treating diabetic erectile dysfunction comprising an extract of mulberry containing C3G.

BACKGROUND ART

Erectile dysfunction disease is considered as a representative urology disease in the field of Andrology. Erectile dysfunction can have psychogenic or organic causes. The organic causes comprise dysfunction of the nervous system, blood vascular system, or endocrine system. Central nervous system disease (e.g. spinal cord injury, multiple sclerosis), peripheral nerve disease (e.g. diabetes, pelvic surgery), hypertension and renal disease have all been associated with erectile dysfunction.

In particular, the frequency of erectile dysfunction in the patients with diabetes is about three times more than ordinary person. Various studies show that 35% to 75% of men with diabetes will develop erectile dysfunction (Fedele, D. et al., Int. J. Epidemiol. 2000, 29, 524-531; Johannes, C. B. et al., J. Urol. 2000, 163, 460-463).

Diabetes harms cavernosal innervation and endothelial function, both of which are important for erectile function, and also decreases nitric oxide production. In addition, hyperglycaemia induces the overproduction of superoxide ($O_2^-$). Corporal apoptosis, resulting from oxidative stress in penile tissues, was found to be a major cause of erectile impairment in diabetic animals.

In general, the treatments for erectile dysfunction comprise psychotherapy, non-surgical therapy and surgical therapy. Non-surgical therapy comprises medicine, priapism induced by intracavernous injection, and vacuum consitriction device. surgical therapy comprises penile vein ligation for venogenic impotence, penile revascularization, and penile prosthesis implantation. Until now, Viagra® is the most effective medicine for treating erectile dysfunction. There have been studied to develop alternatives to Viagra, however, there are no reports about effective medicine to patient with diabetic erectile dysfunction.

Meanwhile, mulberry is a fruit of the *Morus alba* L belonging to the Moraceae family or closely related plants of same genus, and referred to as 'Sangsim' 'Sangsil' 'Osim' or 'Heuksim' in the oriental medicinal system. Mulberries have been used in traditional oriental medicine to treat and prevent diabetes. The root bark of mulberry tree has long been used in oriental medicine for anti-inflammatory, diuretic, antitussive, and antipyretic purposes.

Muberry contains natural pigment C3G, which is one of the most predominant form of anthocyanin. C3G is contained at high level in mulberry and isolated from mulberry easily and stably with high yields, since mulberry has the pigment in all the fruit. Mulberry has 23 times more C3G than grapes and 2.3 times more C3G than colored rice. C3G, which is contained at high level in mulberry, has been demonstrated to exert free radical scavenging and inflammation suppression activities.

With regard to C3G, Korean Patent No. 0601320 discloses the use of C3G for the treatment of hyperlipidemia, and Korean Patent No. 0880876 discloses the use of C3G for the treatment of ischemia-reperfusion injury. In addition, Korean Patent Publication No. 2011-0014401 discloses the use of Rubus Coreanus extract containing C3G for the treatment of gastric antral ulceration. Various medical activities of C3G are reported as above, however, there are no reports or studies about medical effects of C3G on diabetic erectile.

DISCLOSURE

Technical Problem

The present inventors have researched to develop natural therapeutic agents effective for diabetic erectile. As a result, the present inventors demonstrated that C3G, which is contained at high level in mulberry, is effective for improving erectile function in a rat model of diabetes, thereby completing the present invention.

Technical Solution

An object of the present invention is to provide a pharmaceutical composition for preventing or treating diabetic erectile dysfunction comprising C3G (Cyanidin-3-O-β-d-glucopyranoside).

Another object of the present invention is to provide a pharmaceutical composition for preventing or treating diabetic erectile dysfunction comprising an extract of mulberry containing C3G.

Still another object of the present invention is to provide a method for treating diabetic erectile dysfunction, comprising the step of administering an effective amount of a composition comprising C3G into a subject.

Still another object of the present invention is to provide a method for treating diabetic erectile dysfunction, comprising the step of administering an effective amount of an extract of mulberry containing C3G.

Still another object of the present invention is to provide a functional health food for ameliorating diabetic erectile dysfunction comprising C3G.

Still another object of the present invention is to provide a functional health food for ameliorating diabetic erectile dysfunction comprising an extract of mulberry containing C3G.

Still another object of the present invention is to provide a method for ameliorating diabetic erectile dysfunction, comprising the step of feeding a functional health food comprising C3G into a subject.

Still another object of the present invention is to provide a method for ameliorating diabetic erectile dysfunction, comprising the step of feeding a functional health food comprising an extract of mulberry containing C3G into a subject.

Technical Solution

Figure 1:
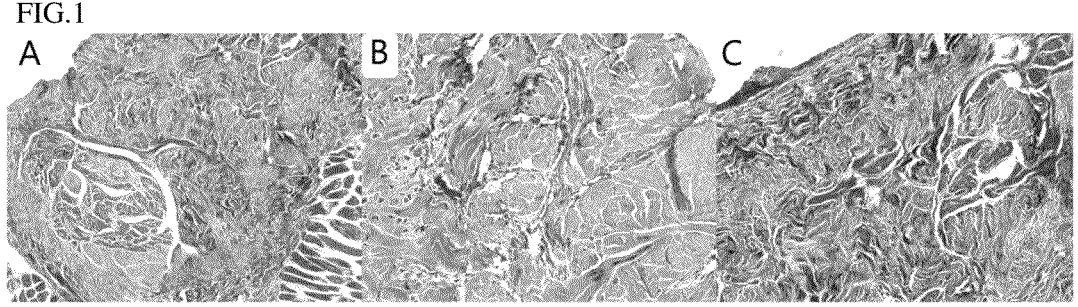
FIG. 1 shows Masson's trichrome staining for collagen (blue) and smooth muscle (red) in corporal tissue of the control (A), diabetes (B), and diabetes treated with C3G (C) groups. Magnification: 200×.

In one aspect, the present invention relates to a pharmaceutical composition for preventing or treating diabetic erectile dysfunction comprising C3G (Cyanidin-3-O-β-d-glucopyranoside).

In another aspect, the present invention relates to a method for treating diabetic erectile dysfunction, comprising the step of administering an effective amount of a composition comprising C3G into a subject.

In the present invention, C3G is the anthocyanin pigment which is the form of cyanidin bound to glucose. C3G of the present invention may be isolated and purified from nature, or obtained commercially.

Preferably, C3G of the present invention may be extracted and isolated from mulberry. Mulberry is a fruit of the *Morus alba* L belonging to the Moraceae family or closely related plants of same genus. Mulberry has 23 times more C3G than grapes and 2.3 times more C3G than colored rice. Furthermore, C3G is contained at high level in mulberry and isolated from mulberry easily and stably with high yields, since mulberry has the pigment in all the fruit.

Further, the active ingredients of the present invention, C3G, are contained in an extract of mulberry in a large amount, and thus the extract of mulberry containing C3G can be also used for the prevention or treatment of diabetic erectile dysfunction.

In still another aspect, therefore, the present invention relates to a pharmaceutical composition for preventing or treating diabetic erectile dysfunction comprising an extract of mulberry containing C3G.

In still another aspect, the present invention relates to a method for treating diabetic erectile dysfunction, comprising the step of administering an effective amount of an extract of mulberry containing C3G.

Any type of the extract of mulberry can be included in the scope of the present invention without particular limitation of extraction method and extraction solvent, as long as the mulberry extract of the present invention contains C3G. Preferably, the mulberry extract of the present invention is understood to include an extract prepared by extracting the mulberry using a solvent selected from the group consisting of water, C3 to C5 ketones, and C1 to C4 linear or branched alcohols, and mixtures thereof, and an extract prepared by fractionating the extract using one or more selected from the group consisting of water, C5 to C7 alkanes, C1 to C4 linear or branched alcohols, methylene chloride, and ethyl acetate. The preferred extraction solvent is water or ethanol. The more preferred extraction solvent is 0.1% citric acid and 70% ethanol.

The mulberry extract of the present invention may be prepared according to the typical preparation methods of plant extracts, and preferably prepared by hot water extraction, pressure extraction, reflux extraction, warm immersion extraction, ultrasonic extraction or the like, but the method is not limited thereto. In addition, the extract prepared as above may be concentrated or the solvent may be removed therefrom by performing filtration under reduced pressure or by further performing concentration and/or freeze-drying. Therefore, the term "mulberry extract", as used herein, includes a dry extract that is dried by the typical method and a liquid extract or solid extract that is concentrated by removing the extraction solvent.

In the present invention, diabetic erectile dysfunction refers to a man's inability to obtain or sustain an erection due to neuropathy or vasculopathy of tissue of corpus cavernosum penis which are indicated under diabetes. Thus, the composition of the present invention may be used for a subject having diabetes mellitus, in particular, type 1 diabetes or type 2 diabetes.

The prophylactic or therapeutic activities of the composition comprising C3G of the present invention on diabetic erectile dysfunction have been directly demonstrated in a rat model of diabetic erectile dysfunction.

In the specific Example of the present invention, the intracavernosal pressure (ICP) decreased in the diabete rat model but it significantly improved when C3G extracted from mulberry pigments is treated (Table 2 in Examples). In general, the increase of the intracavernosal pressure can make penis easy to erect. When electrical stimulation was given to the cavernosal nerve of an experimental model of diabetes in order to simulate the process of erection, ICP and ICP/MAP (intracavernosal pressure/mean arterial pressure) decreased in the diabetic rat. When C3G was administered into the diabetic rat, however, peak ICP and ICP/MAP significantly increased.

In addition, the present inventors found that C3G can improve function of penis tissue by increasing function of smooth muscle (FIG. 1). In the result of Masson's trichrome staining, smooth muscle content increased and collagen content decreased in the C3G treatment group.

Figure 2:
FIG. 2 shows immunohistochemical in situ TUNEL detection of apoptosis in corporal tissue of the control (A), diabetes (B), and diabetes treated with C3G (C) groups. Cells undergoing apoptosis, called apoptotic bodies, show as black or dark brown in the TUNEL assay, while living cells are shown as lighter dots. Magnification: 400×.

In addition, the present inventors found that C3G can improve erectile function by minimizing cell apoptosis in rat model of diabetic erectile dysfunction (FIG. 2). In the result of TUNEL assay for apoptosis, compared with the diabetic rat group, significantly fewer cells stained positively in the C3G administration group. This means that the cell apoptosis in the cavernosum decreased in the C3G administration group.

Figure 3:
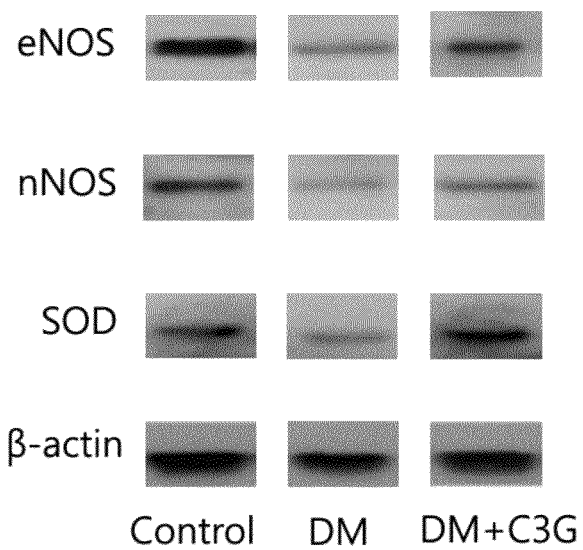
FIG. 3 shows expression levels of eNOS, nNOS and SOD. (A) Western blot analysis of eNOS, nNOS and SOD in corporal tissue. (B) Densitometric analysis relative to beta actin. The data are expressed as the mean±SD. * significant difference between the control and DM groups; ** significant difference between the DM and C3G-treated DM groups.
Figure 3:
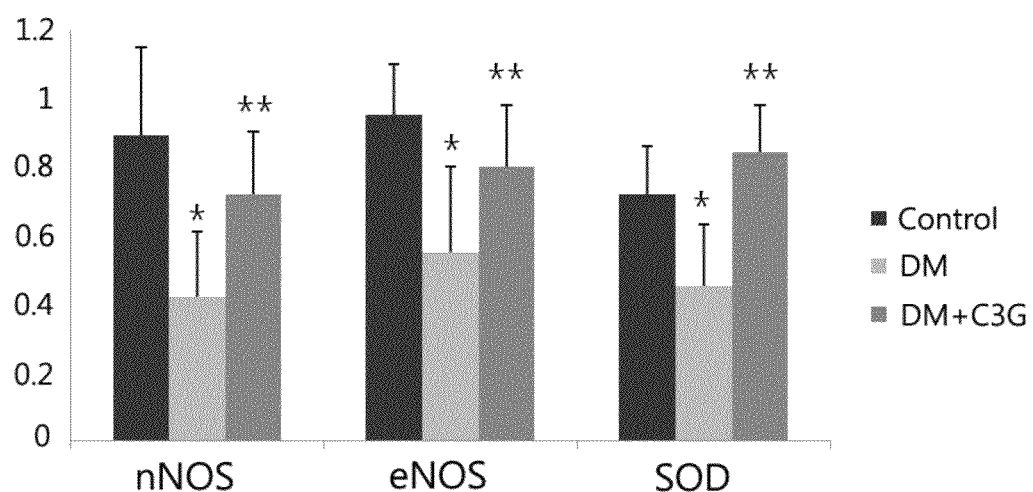

In addition, the present inventors found that C3G can promote the expression of eNOS and nNOS proteins (FIGS. 3A and B). Nitric oxide (NO) is an important neurotransmitter mediating smooth muscle relaxation. NO associated with mechanism of election is produced by neuronal NOS (nNOS) and endothelial NOS (eNOS). With respect to C3G, the expression of eNOS and nNOS, which had been decreased by diabetes, showed subsequent increases, strongly indicating that C3G increases NO bioactivity thereby improving erectile function.

In the present invention, it was demonstrated that C3G down-regulated the expression of 8-OHdG(8-hydroxy-2'-deoxyguanosine) as a marker of oxidative injury of DNA of testis tissues and up-regulated the expression of SOD. These results show that C3G decreases oxidative injury of testis tissues under the oxidative stress circumstance and recovers cells, thereby inhibiting the progression of erectile dysfunction (FIGS. 3A and B).

Therefore, the present invention is the first to suggest that C3G has a potency to improve and protect erectile function by minimizing corporal apoptosis in a rat model of diabetic erectile dysfunction.

The composition of the present invention may further include nutrients, vitamins, electrolytes, a flavoring agent, a coloring agent, an extender, pectic acid and salts thereof, alginic acid and salts thereof, organic acid, a protective colloid thickener, a PH adjuster, a stabilizer, a preservative, glycerin, alcohol, a carbonating agent used for a carbonated drink, in addition to the active ingredient C3G or the mulberry extract including the same. These ingredients may be added singly or in combination. Preferably, the content of the additional ingredient ranges from 0.1 to 20% by weight based on 100% by weight of C3G or the mulberry extract including the same, or ranges from 100 to 10,000,000% by weight based on 100% by weight of licoricidin, but is not limited thereto.

The content of the C3G or mulberry extract in the composition may be properly adjusted depending on disease severity, symptom progression, patient's status, etc. For example, the content is 0.0001 to 99.9% by weight, preferably 0.001 to 50% by weight, based on the total weight of the composition, but is not limited thereto. The content is based on the solvent-removed dry weight.

The composition may further include an adequate carrier, excipient or diluent commonly used for the preparation of pharmaceutical compositions, and it may be prepared into oral preparations such as powder, granule, tablet, capsule, suspension, emulsion, syrup, aerosol or the like, and preparations for external application, suppository or sterile injection solution according to common methods.

When the composition is formulated, a commonly used diluent or excipient such as filler, extender, binder, wetting agent, disintegrant, surfactant or the like may be used. Solid formulations for oral administration include tablet, pill, powder, granule, capsule or the like, and these solid formulations may include at least one excipient and/or lubricant. Liquid formulations for oral administration include suspension, liquid for internal use, emulsion, syrup or the like, and various excipients such as wetting agent, sweetener, aromatic, preservative or the like may be included, in addition to a commonly used simple diluent such as water and liquid paraffin. Formulations for parenteral administration include sterile aqueous solution, non-aqueous solution, suspension, emulsion, lyophilized preparation and suppository.

A preferred administration dose of the composition varies depending on the patient's physical conditions and body weight, severity of disease, formulation type, administration route and administration period, and may be determined adequately by those skilled in the art. To attain more desirable effect, the composition of the present invention may be administered at a daily dosage of 0.1 to 20 mg/kg based on the active ingredient, but is not limited thereto. The administration may be performed once or several times a day. The composition of the present invention may be administered to animals, preferably mammals including human, via various routes. All administration routes may be contemplated, for example, oral, intravenous, intramuscular, and subcutaneous routes. In pharmaceutical dosage form, the composition of the present invention may be administered in the form of pharmaceutically acceptable salts thereof, or it may be also used alone or in appropriate association, as well as in combination with other pharmaceutically active compounds.

In still another aspect, the present invention relates to a functional health food for ameliorating diabetic erectile dysfunction comprising C3G.

In still another aspect, the present invention relates to a method for ameliorating diabetic erectile dysfunction, comprising the step of feeding a functional health food comprising C3G into a subject.

In still another aspect, the present invention relates to a functional health food for ameliorating diabetic erectile dysfunction comprising an extract of mulberry containing C3G.

In still another aspect, the present invention relates to a method for ameliorating diabetic erectile dysfunction, comprising the step of feeding a functional health food comprising an extract of mulberry containing C3G into a subject.

As used herein, the food means any natural or synthetic product containing one or more nutrients, and preferably those processed to be edible, and it commonly includes a variety of foods, functional health foods, beverages, food additives, and beverage additives. Examples of the food include various foods, beverages, gum, tea, vitamin complex, and functional health foods. Additionally, the food of the present invention includes special nutrient foods (e.g., formula milk, foods for infants and young children, etc.), meat products, fish products, bean curds, curds, noodles (e.g., instant noodle, other noodles, etc.), health food supplements, seasoning foods (e.g., soy sauce, soybean paste, hot pepper paste, mixed soybean paste, etc.), sauces, snacks, dairy products (e.g., fermented milk products, cheese, etc.), other processed foods, kimchi, preserved food products (e.g., kimchi, sliced vegetables preserved in soy sauce, etc.), beverages (e.g., fruit beverages, vegetable beverages, soy milk, fermented beverages, ice cream, etc.), natural seasoning (e.g., instant noodle base, etc.), vitamin complex, alcoholic beverages, liquor, and other health food supplements, but is not limited thereto. The functional health foods, beverages, food additives, or beverage additives may be prepared by the typical method.

The functional health food may include a sitologically acceptable food additive, and further include an adequate carrier, excipient or diluent commonly used for the preparation of functional foods.

Further, the food may include 0.00001% by weight to 50% by weight of the C3G or mulberry, based on the total weight of the food, and if the food is a beverage, it may include 0.001 g to 50 g, and preferably 0.01 g to 10 g thereof, based on 100 ml of the food, but is not limited thereto.

MODE FOR INVENTION

Hereinafter, the present invention will be described in detail with reference to Examples. However, these Examples are for illustrative purposes only, and the invention is not intended to be limited by these Examples.

Example 1

Preparation of Natural Pigment with Mulberry Fruit

C3G concentration materials, which were extracted from mulberry fruit pigment, used in our experiments were supplied by the Rural Development Administration, Suwon, Republic of Korea. In brief, in order to extract C3G from fresh mulberry, frozen mulberry and freeze-dried mulberry, 0.1% citric acid and 70% ethanol were added to those mulberries and filtered. The solvents of extraction were added followed by mashing mulberries with hand or using shaking incubator at 4° C. for 24 hours. The extracted filtrate was isolated and concentrated by using Scale Rotary Evaporator at 40° C., 85mbar and 50rpm, then the concentrates were prepared (Kim H B, et al. Korean J Crop Sci. 2011; 56:18-22).

Example 2

Animal Groups and Treatment Protocol

Thirty-six 12-wk-old male Sprague-Dawley rats were treated under a protocol approved by the Institutional Animal Care and Use Committee (CUMC-2010-0137-02) and handled according to NIH guidelines. Rats were divided equally into three groups (n=12 in each): control, diabetes (DM), and diabetes with C3G concentration materials treatment (DM+C3G). All rats in the DM and DM+C3G groups received a single intraperitoneal injection of streptozotocin (50 mg/kg). Blood glucose and body weight were monitored weekly and significant diabetes (serum glucose >250 mg/dl) was confirmed in all rats within 1 wk. The diabetic serum level was maintained throughout the experiment. Four weeks after the induction of diabetes, rats in the DM+C3G group were treated with daily oral C3G (10 mg/kg) dissolved in water for 8 weeks. After the 12 weeks, intracavernosal pressure measurement (ICP) was performed, and after ICP measurement, the skin-denuded middle part of the penile shafts was cut and fixed overnight in 10% formalin, washed, and stored in 70% alcohol at 4° C. until processed for paraffin-embedded tissue sectioning (5 μm). Tissue was stored at −80° C. until processing.

Example 3

Intracavernosal Pressure measurement

Rats were anaesthetized with an intraperitoneal injection of 0.2 mL tiletamine (Zoletil®). With the rat in the supine position, the penis was dissected and the corpus cavernosum and crus of the penis were exposed. A low, midline abdominal incision was made to access the pelvis, and the pelvic ganglion lateral to the right prostate was exposed. For the measurement of ICP, a heparinized 23G butterfly needle was inserted in the corpus cavernosum of penile proximal portion after the penile skin was degloved and the corpus cavernosum identified. Then, a bipolar electrical stimulator was placed on the ganglion to stimulate the cavernosal nerve for 50 seconds at 10V and 2.4 mA for 0.5 ms. The cavernosal nerve stimulation was conducted at least three times and the interval between stimulations was maintained for more than 10 minutes. Both mean arterial pressure (MAP) and ICP were continuously monitored during electrical stimulation. Comparisons were made for ICP/MAP and area under the curve corresponding to the duration of electrical stimulation. After the stimulation test, the corpus cavernosum was removed and divided into two. The first part was cryopreserved in liquid nitrogen and the other part was fixed in formalin.

Example 4

TUNEL (Terminal Deoxynucleotidyl Transferase Mediated dUTP Nick End Labeling) Assay To assess apoptosis in the corpora tissues, the terminal deoxynucleotidyl transferase mediated dUTP nick end labeling (TUNEL) assay was performed using Apop Tag In Situ Apoptosis Detection Kits (Millipore Co., MA, US). Tissue preparation for the detection of apoptotic bodies was done according to the manufacturer's protocol. After the TUNEL assay, testis tissue sections were examined by light microscopy. The number of cells positive for the TUNEL assay was counted and the difference among the groups was assessed. For the count of cells positive for the TUNEL assay, 5 sites were selected randomly from a slide of each group, and the number of cells positive for the TUNEL assay was counted as the average of 5 sites under a light microscope at 400× magnification.

Example 5

Masson's Trichrome Staining

After ICP, the skin denuded middle part of the penile shafts were fixed overnight in 10% formalin, washed, and stored in 70% alcohol at 4° C. until processed for paraffin-embedded tissue sectioning (5 μm). The cavernosal tissue was obtained for the Masson's trichrome staining. After staining, the color distribution of the muscle tissue was approximated by using the Adobe Photoshop CS 8.0. After the entire color distribution of the image was calculated, we selected the muscle tissue distribution, expressed as the color red. There were somewhat standard deviations in our calculation because of color overlays and ambiguity of the color spectrum of the muscle tissues.

Example 6 eNOS, nNOS and SOD Protein Expression Tests: Western Blot

A cavernosal strip was homogenized individually in a buffer solution of 0.32M sucrose, 0.2M Hepes, (pH 7.4), 1 mM EDTA(ethylenediaminetetraacetic acid), 1 mM DTT (dithiothreitol), 10 μg/mL leupeptin, 2 μg/mL aprotinin, 1 μg/mL pepstatin, 10 μg/mL trypsin inhibitor, and 1 mM PMS-F(phenylmethylsulfonyl fluoride).

The homogenized buffer solution was placed on ice for 15 min and centrifuged at 4° C. for 13,000 rpm for 15 minutes. The supernatant solution was separated. 30 μg of the quantitative protein was denatured at 95° C. for 5 min and electrophoresis was performed on a 12% discontinuous sodium dodecylsulfate-polyacrylamide gel (SDS-PAGE). The proteins were then electroblotted onto a 0.2 μm polyvinylidenedifluoride (PVDF, Amershambioscience, USA) membrane for 150 minutes at 25V. The membranes were reacted with blocking buffer (5% skim milk in TBS-T buffer) for 30 minutes at the ambient temperature and then incubated overnight at 4° C. with anti-endothelial NOS (eNOS), (140 KDa/1:100/BD Biosciences, USA), anti-neuronal NOS (nNOS) (155 KDa/1:1000/BD Biosciences, USA), or anti-SOD antibodies (155 KDa/1:5000/Abcam plc). After washing with 1× TTBS, membranes were incubated at room temperature for 1 hour with anti-mouse IgG for nNOS, anti-rabbit IgG for eNOS, and superoxide dismutase (SOD) (Zymed Laboratories, USA) diluted 1:1,000. The membranes were then was washed again with TTBS 6 times with an interval of 5 minutes between each washing. Chemiluminescence was detected using enhanced chemiluminescence Western blotting detection reagents and densitometric assessment of the bands on the autoradiogram was performed using Bio1D software (version 97; Vilber Lourmat, France).

Example 7

Measurement of 8-OHdG (8-hydroxy-2-deoxyguanosine)

Oxidative stress in corpora tissues was evaluated by quantifying the levels of 8-hydroxy-2-deoxyguanosine (8-OHdG) as oxidatively modified DNA. Using DNeasy Blood & Tissue kit (Qiagen, Valencia, Calif., USA), total DNA was extracted from the testis according to the manufacturer's instructions. Levels of 8-OHdG were measured with a DNA oxidation kit (Highly Sensitive 8-OHdG Check ELISA; Japan Institute for the Control of Aging, Fukuroi, Japan) according to the manufacturer's protocol. The 8-OHdG standard (0.5-40 ng/mL) or 15 to 20 μg of DNA purified from the testis was incubated for 1 hour with a monoclonal antibody against 8-OHdG in a microtiter plate precoated with 8-OHdG. After the final color was developed with the addition of 3,3',5,5'-tetramethylbenzidine, absorbance was measured at 450 nm. Tissue sample concentration was calculated from a standard curve and was corrected for DNA concentration.

Results

1. General Features of Diabetes

Table 1 describes changes in body weight and blood glucose levels of the three groups. During the experiment, the serum glucose levels of the two DM groups were maintained and showed no significant difference. With respect to the body weight of DM groups, it was significantly decreased compared with the control group.

TABLE 1

|  |  | Pre-DM induction | 4 wk | 8 wk | 12 wk |
|---|---|---|---|---|---|
| Body weight (g) | Control | 408 ± 32 | 484 ± 47 | 647 ± 76 | 675 ± 92 |
|  | DM | 415 ± 23 | 384 ± 55* | 422 ± 74* | 467 ± 97* |
|  | DM + C3G | 441 ± 29 | 418 ± 78* | 408 ± 68* | 441 ± 85* |
| Serum glucose (mg/dl) | Control | 120 ± 7 | 123 ± 5 | 128 ± 10 | 122 ± 2 |
|  | DM | 127 ± 10 | 469 ± 70* | 532 ± 42* | 501 ± 71* |
|  | DM + C3G | 141 ± 13 | 462 ± 90* | 448 ± 143* | 469 ± 163* |

*Significant statistical difference ($p < 0.05$) compared to the control

2. In Vivo Assessment of Erectile Function

Table 2 describes intracavernosal pressure in response to electrical stimulation of the cavernous nerve in rats from each experimental group. In particular, Peak ICP and ICP/MAP ratios decreased in the DM group compared with the control group and significantly improved in the C3G treatment group. The control and DM+C3G groups had statistically similar Peak ICP and ICP/MAP ratios, which were significantly higher than those of the DM group.

TABLE 2

|  | Control | DM | DM + C3G | p-value |
|---|---|---|---|---|
| Peak ICP | 83.3 ± 1.9 | 35.4 ± 4.5 | 58.0 ± 4.6 | 0.023† 0.039⁺ 0.004∥ |
| MAP | 108.5 ± 3.4 | 109.4 ± 2.8 | 104.6 ± 4.5 |  |
| ICP/MAP ratio | 0.77 ± 0.05 | 0.32 ± 0.06 | 0.55 ± 0.11 | 0.031† <0.001⁺ 0.023∥ |

†One-way ANOVA test, overall comparison;
⁺comparison between control and DM groups; and
∥comparison between DM and DM + C3G groups.

3. Masson's Trichrome Staining

In comparison with the control group, smooth muscle content of corpora tissues was decreased and collagen deposition was increased in the DM group and smooth muscle content increased and collagen content decreased in the C3G treatment group (FIG. 1). The muscle/collagen ratio was 27.3±3.0 (control), 10.6±4.6 (DM), 21.8±1.7 (DM+C3G). A significant decrease in muscle/collagen ratio was shown in the DM group compared with control group, C3G treatment significantly increased muscle/collagen ratio.

4. TUNEL Assay for Apoptosis

The mean apoptotic indices±standard deviation of the three groups as detected by the TUNEL assay were 15.3±3.0 (control), 39.6±4.6 (DM), and 21.3±1.7 (DM+C3G). The DM group showed a higher mean apoptotic index than that of the control ($p<0.05$). Compared with the DM group, significantly fewer cells stained positively in the TUNEL assay in the C3G administration groups ($p<0.05$). Representative pictures are shown in FIG. 2.

6. Expression of eNOS and nNOS Proteins

In all groups, the expression of NOS against actin was different and so we needed the correction to compare the expression of NOS. We corrected the expression of NOS against actin as 100 and compared the expression of NOS. eNOS and nNOS proteins were decreased according to western blot analysis in the DM group as compared with the control group, and levels increased in the C3G treatment group as revealed in the densitogram (FIGS. 3A and B).

7. Measurement of Oxidative Stress in Corpora Tissues

Levels of oxidative stress in corpora tissues were assessed quantitatively by measuring 8-OHdG in the corpora tissue by ELISA. In the normal group, DM group, and DM+C3G group, 8-OHdG was 0.140±0.13, 0.917±0.247, 0.626±0.423, respectively. A significant increase in oxidative stress was shown in the DM group compared with the normal control group ($p<0.05$). In the DM group treated with C3G; however, oxidative stress was statistically significantly reduced compared with DM group ($p<0.05$). With respect to SOD, western blot analysis revealed a significant decrease in DM group compared with the control group; however, it was expressed more in the DM group treated with C3G than in the control group (FIGS. 3A and B).

8. Conclusion

C3G can improve erectile function by minimizing corporal apoptosis. The present invention is the first to suggest that C3G has a potency to improve and protect erectile function in a rat model of diabetic erectile dysfunction.

INDUSTRIAL APPLICABILITY

The composition of the present invention, comprising C3G or an extract of mulberry containing C3G, is a safe, natural composition having improved therapeutic effect on diabetic erectile dysfunction without any side effect or toxicity. Therefore, the composition can be applied more safely and effectively to treating diabetic erectile dysfunction.

The invention claimed is:

1. A method for treating diabetic erectile dysfunction, comprising the step of administering an effective amount of C3G (Cyanidin-3-O-β-d-glucopyranoside) into a subject.

2. The method according to claim 1, wherein the C3G is administered with a pharmaceutically acceptable carrier.

3. The method according to claim 1, wherein the C3G is purified C3G.

4. The method according to claim 3, wherein the C3G is extracted and isolated from mulberry.

5. A method for ameliorating diabetic erectile dysfunction, comprising the step of administering C3G (Cyanidin-3-O-β-d-glucopyranoside) into a subject.

6. The method according to claim 5, wherein the C3G is administered with a sitologically acceptable food additive.

7. The method according to claim 5, wherein the C3G is purified C3G.

8. The method according to claim 7, wherein the C3G is extracted and isolated from mulberry.

* * * * *